US00PP36753P2

(12) United States Plant Patent
Bédard

(10) Patent No.: US PP36,753 P2
(45) Date of Patent: Jun. 24, 2025

(54) FLORIBUNDA ROSE PLANT NAMED 'WEKaltbeba'

(50) Latin Name: *Rosa hybrida*
Varietal Denomination: WEKaltbeba

(71) Applicant: Early Morning LLC, Lawrenceburg, IN (US)

(72) Inventor: Christian Bédard, Rancho Cucamonga, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 18/957,222

(22) Filed: Nov. 22, 2024

(51) Int. Cl.
*A01H 5/02* (2018.01)
*A01H 6/74* (2018.01)

(52) U.S. Cl.
USPC ..... Plt./147
CPC ..... *A01H 6/749* (2018.05)

(58) Field of Classification Search
USPC ..... Plt./147, 148, 149
CPC ..... A01H 5/0222
See application file for complete search history.

(56) References Cited

U.S. PATENT DOCUMENTS

| | | | |
|---|---|---|---|
| PP8,494 | P | 12/1993 | Tracy |
| PP9,389 | P | 12/1995 | Winchel |
| PP22,469 | P2 | 1/2012 | Carruth |
| PP22,571 | P2 | 3/2012 | Carruth |
| PP23,324 | P2 | 1/2013 | Bedard |
| PP23,692 | P3 | 7/2013 | Bedard |
| PP29,273 | P2 | 5/2018 | Fryer |

OTHER PUBLICATIONS

Weeks Roses: In Love Again, Wholesale Rose Catalog, Weeks Roses, 2025. Retrieved from the Internet: <URL:http://www.weeksroses.com/downloads/Catalogs_Digital/_WR25_Catalog_Digital.pdf>, 76 pages.

*Primary Examiner* — Kent L Bell
(74) *Attorney, Agent, or Firm* — McKee, Voorhees & Sease, PLC

(57) ABSTRACT

A new variety of Floribunda rose suitable for garden decoration, having flowers of coral pink coloration.

1 Drawing Sheet

Classification: The present disclosure relates to a new *Rosa hybrida* plant.

Variety denomination: The new plant has the varietal denomination 'WEKaltbeba'.

BACKGROUND OF THE INVENTION

This invention relates to a new and distinct variety of Floribunda Rose. It has as its seed parent the variety known as 'WEKcofbunk' (U.S. Plant Pat. No. 23,324) and as its pollen parent the variety known as 'WEKwisogoma' (U.S. Plant Pat. No. 23,692).

SUMMARY OF THE INVENTION

Among the features which distinguish the new variety from other presently available and commercial rose cultivars known to the applicant are the following combinations of characteristics: its elegant flowers of coral pink coloration, its abundant blooms and its excellent color stability throughout the life of the flower. The plant has an upright moderately spreading growing habit, suitable for outdoor garden decoration.

Asexual reproduction of the new variety by budding as performed in Kern County, California, shows that the foregoing and other distinguishing characteristics come true to form and are established and transmitted through succeeding asexual propagations. 'WEKaltbeba' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKcofbunk' by the following combination of characteristics: whereas 'WEKaltbeba' bears very double flowers (about 37 to 69 petals) of coral pink coloration, 'WEKcofbunk' bears semi-double flowers of twinkling brilliant orange coloration with significantly lesser petalage (about 12 to 17 petals). The new variety bears medium to somewhat large flowers (about 7.0 to about 11.7 cm. in diameter), whereas the seed parent bears significantly smaller flowers (about 5.4 to 6.9 cm. in diameter).

The new variety may be distinguished from its pollen parent, 'WEKwisogoma' by the following combination of characteristics: whereas 'WEKaltbeba' bears very double flowers (about 37 to 69 petals) of coral pink coloration, 'WEKwisogoma' bears double flowers of incandescent pink coloration with significantly lesser petalage (about 15 to 24 petals). The new variety bears medium to somewhat large flowers (about 7.0 to about 11.7 cm. in diameter), whereas the pollen parent bears significantly smaller flowers (about 5.1 to about 6.8 cm. in diameter).

COMPARISON WITH THE CLOSEST COMMERCIALLY AVAILABLE CULTIVAR

The new variety may be distinguished from its closest commercially available cultivar, 'KORtekcho' (U.S. Plant Pat. No. 25,993) by the following combination of characteristics: whereas 'WEKaltbeba' bears medium to somewhat large (about 7.0 to about 11.7 cm. in diameter) very double flowers (about 37 to 69 petals), 'KORtekcho' bears significantly smaller flowers (average 7.5 cm. in diameter) with significantly heavier petalage (approximately 75 petals under normal conditions). The new variety has a slight fruity fragrance, whereas the closest commercially available cultivar has a strong fragrance with citron, elderberry and fruit notes.

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, California in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, California in the month of November. Phenotypic expression may vary with environmental, cultural and climatic conditions, as well as differences in conditions of light and soil.

FLOWER

The new variety sometimes bears its flowers singly, sometimes in clusters of two to six or more per stem. Flowers may be borne in regular rounded clusters on strong moderately short to medium length stems (about 13 to about 50 cm.). The cluster ranges from about 8.5 to about 15.5 cm. in diameter. Outdoors, the plant blooms abundantly and nearly continuously during the growing season. The flowers have a slight fruity fragrance.

BUD

The peduncle is about 1.5 to about 7.5 cm. in length, of somewhat slender to average caliper (about 0.2 to about 0.4 cm. in diameter), and usually erect to somewhat stiff. It is moderately smooth, with few stipitate glands, and few hairs. Peduncle color is between 146C and 152B sometimes moderately suffused, especially on the side exposed to the sun, with between 187B and 187A.

Before the calyx breaks, the bud is about 1.1 to about 2.1 cm. in diameter at the widest point, about 1.1 to about 1.9 cm. in length, and globular in shape. The surface of the bud bears between 13 to 15 foliaceous appendages with some stipitate glands and many hairs, usually with slender entire foliaceous parts extending beyond the tip of the bud about ½ or more of its length. Bud color is between 137C and 148B sometimes moderately suffused, especially on the side exposed to the sun, with between 187B and 187A.

The sepals are 5 per flower, about 1.5 to about 3.2 cm. in length and about 0.7 to about 1.4 cm. in width at the widest point. The outer surface color of the sepal is between 137C and 148B sometimes moderately suffused, especially on the side exposed to the sun, with between 187B and 187A. The outer surface of the sepal is somewhat rough and bears between 0 to 7 foliaceous appendages with some stipitate glands, and many hairs. The inner surface color of the sepal is near 146D broadly bordered by near 137B. After the sepals open, the inner surface color is often lightly suffused, especially on the area exposed to the sun, with between 187D and 187C. The inner surface of the sepal is covered with fine wooly tomentum; sepal margins are entire and lined with some stipitate glands and many hairs. The sepals are moderately permanent, and usually spear-shaped in shape with acute apices.

The receptacle of the flower is of short length (about 0.3 to about 0.6 cm.) and moderately thin to average in caliper (about 0.6 to about 1.3 cm. in diameter). The receptacle is funnel shaped in form. Its surface is smooth with very few hairs and with moderately thin fleshy walls. The receptacle color is between 146C and 148B.

As the petals open (after the calyx breaks), the bud is about 2.0 to about 2.3 cm. in diameter at the widest point, about 1.7 to about 3.0 cm. in length, and globular to somewhat ovoid in form. The color of the under surfaces of the newly opened petals is between 55A and 48C. At the point where the petal attaches, there is a somewhat large zone of between 154C and 1C. The color of the upper surfaces of the newly opened petals is between 48C and 52C. At the point where the petal attaches, there is a moderately large zone of between 154C and 1C.

BLOOM

When fully open, the bloom ranges from about 7.0 to about 11.7 cm. in diameter. Petalage is very double with about 37 to 69 petals and about 2 to 15 petaloids irregularly arranged. When partially open, the bloom form is moderately globular to somewhat cupped, and the petals are tightly spiraled to cupped with petal edges somewhat reflexed outward. When fully open, the bloom form is more cupped, and the petals are loosely cupped with petal edges somewhat reflexed outward.

PETALS

The substance of the petals is moderately heavy and of medium thickness, with upper surfaces somewhat satiny and under surfaces moderately shiny. The petals are about 2.7 to about 4.6 cm. in length and about 2.1 to about 5.3 cm. in width at the widest point. Petal margins are entire.

The outer petals are nearly rounded to somewhat obovate in shape with rounded apices.

The inner petals are broadly obovate to somewhat oblanceolate in shape with rounded apices.

Petaloids are about 0.8 to about 4.0 cm. in length and about 0.4 to about 3.0 cm. in width at the widest point. Petaloids are irregularly shaped somewhat oblanceolate to subulate with rounded apices.

NEWLY OPENED FLOWER

The under-surface color of the outer petals is between 63C and 58C. At the point where the petal attaches, there is a moderately large zone of between 3D and 2C. The upper surface color of the outer petals is between 66D and 62A. At the point where the petal attaches, there is a large zone of between 7D and 5C.

The under-surface color of the intermediate and inner petals is between 54B and 58C. The upper surface color of the intermediate and inner petals is between 54A and 58C.

The under and upper surface colors of the petaloids are similar in coloration to the upper and under surfaces of the intermediate and inner petals.

The general tonality of the newly opened flower is between 54A and 58C.

THREE-DAY-OLD FLOWER

The under-surface color of the outer, intermediate and inner petals is between 66D and 62A. At the point where the petal attaches, there is a moderately large zone of near 4D. The upper surface color of the outer, intermediate and inner petals is between 66D and 62A. At the point where the petal attaches, there is a large zone of between 3D and 2C.

The under and upper surface colors of the petaloids are similar in coloration to the upper and under surfaces of the intermediate and inner petals.

The general tonality of the three-day-old flower is between 66D and 62A.

On the spent bloom, the petals usually drop off cleanly.

In November in Wasco, California, blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 125) and are arranged regularly about the pistils; a few are mixed with petaloids. The filaments are of moderately short to medium length (about 0.3 to about 0.9 cm.) most with anthers. Filaments are between 13B and 14B in color. The anthers are of moderately small to medium size for the class and all open approximately at the same time. Anther color when immature is near 22A on the external part and near 13D on the internal part. Anther color at maturity is near 164C on the external part and near 200A on the internal part. Pollen is abundant and between 21C and 21B in color.

FEMALE REPRODUCTIVE ORGANS

Pistils vary in number (average about 145). The styles are moderately even, average to somewhat long in length (about 0.4 to about 0.8 cm.), moderately thin in caliper, and loosely bunched. Stigma color is between 11A and 8A. Style color is between 1C and 2C often heavily suffused near the top with between 53B and 53C. Ovaries are usually all enclosed in the calyx. The ovaries are of somewhat small to medium size and between 159A and 159B in color.

Hips are of moderately short to average length (about 1.2 to about 2.1 cm.), funnel shaped to somewhat globular with a flat top, and between 31A and 34B in color when ripe. The hip surface is smooth with thick fleshy walls.

The seeds are irregularly rounded, smooth in texture, approximately 7 to about 18 per hip, about 0.2 to about 0.5 cm. in diameter at the widest point and between 164D and 165D in color.

FOLIAGE

The compound leaves are usually comprised of three to seven leaflets and are borne abundantly. The seven-leaflet leaves are about 12.0 to about 17.2 cm. in length and about 7.6 to about 11.7 cm. in width at the widest point, moderately leathery to somewhat crisp in texture on both sides, and glossy in finish on the upper side and somewhat semi-glossy to matte in finish on the underside. The leaves have a pinnate venation pattern. The terminal leaflets are about 5.0 to about 7.5 cm. in length and about 3.5 to about 5.2 cm. in width at the widest point, shaped ovate with acute apices and rounded bases. Their margins are usually simply serrate.

The upper surface color of the mature leaf is between 139A and 147A. The under-surface color of the mature leaf is between 147B and 147C. The under and upper colors of the leaf veins on the mature leaf are similar in coloration to the upper and under surfaces colors of the mature leaf. The upper surface color of the young leaf is between 137B and 137A, often moderately suffused with between 187A and 187B. The under-surface color of the young leaf is between 147B and 147C, often moderately suffused with between 187A and 187B. The under and upper colors of the leaf veins on the young leaf are similar in coloration to the upper and under surfaces colors of the young leaf.

The rachis is about 4.8 to about 7.7 cm. in length, about 0.1 to about 0.2 cm in width at the widest point, and moderately rough. The upper side is deeply grooved with some hairs and few stipitate glands on the edges of the grooves. The under side of the rachis is moderately rough with some hairs, few stipitate glands and few small prickles. The rachis color is near 145B on the under side and near 137C on the upper side, often moderately suffused on the young leaves with between 187B and 187C.

The stipules are about 1.0 to about 1.7 cm. in length and of medium width (about 0.5 to about 0.7 cm.) with medium to moderately long straight points that usually turn out at an angle of more than 45 degrees and sometimes recurve toward the stem. The under and upper surface color of the stipule is between 137A and 137B. The upper and under surfaces of the stipules are smooth in texture.

The petiole is average in caliper and moderately rough. The upper side is deeply grooved with some hairs and few stipitate glands on the edges of the grooves. The under side of the petiole is moderately rough with some hairs, few stipitate glands and few small prickles. The petiole is about 0.3 to about 1.3 cm. in length and about 0.1 to about 0.2 cm in width at the widest point. The petiole color is near 145B on the underside and near 137C on the upper side, often moderately suffused on the young leaves with between 187B and 187C.

The plant displays an above average degree of resistance to powdery mildew (*Sphaerotheca pannosa*), downy mildew (*Peronospora sparsa*), black spot (*Diplocarpon rosae*) and rust (*Phragmidium* sp.) as compared to other commercial varieties grown under comparable conditions in Wasco, California. The plant's winter hardiness and drought/heat tolerance are yet to be determined.

GROWTH

The plant has an upright moderately spreading medium height to somewhat tall growing habit (about 78 to about 152 cm. in height and about 102 to about 128 cm. spread at the widest point), with full branching. It displays vigorous growth and the canes are of medium to somewhat heavy caliper for the class (about 1.2 to about 2.0 cm. in diameter at the widest point).

The color of the major stems is between 146B and 146C. The major stems are rough in texture and they bear some large prickles that are about 0.5 to about 1.1 cm. in length. The large prickles are angled slightly downward with a medium length somewhat narrow oval base; prickle color is between 164B and 165C often moderately suffused with between 201B and 201C. The major stem bears few small prickles of similar shape and coloration.

The color of the branches is between 146B and 146C. The branches are rough in texture and they bear some large prickles which are of similar size and shape to the large prickles on the major stems; prickle color is between 161B and 161A sometimes lightly suffused with near 187D. The branches bear few small prickles of similar shape and coloration.

The color of the new shoots is between 146B and 147B often moderately suffused with between 187B and 187C. The new shoots are rough in texture and they bear some large prickles which are of similar size and shape to the large prickles on the major stems; prickle color is between 148B and 147C often heavily suffused with between 187C and 187D. The shoots bear few small prickles of similar shape and coloration.

I claim:

1. A new and distinct Floribunda rose plant of the variety designated 'WEKaltbeba' substantially as described and illustrated herein.

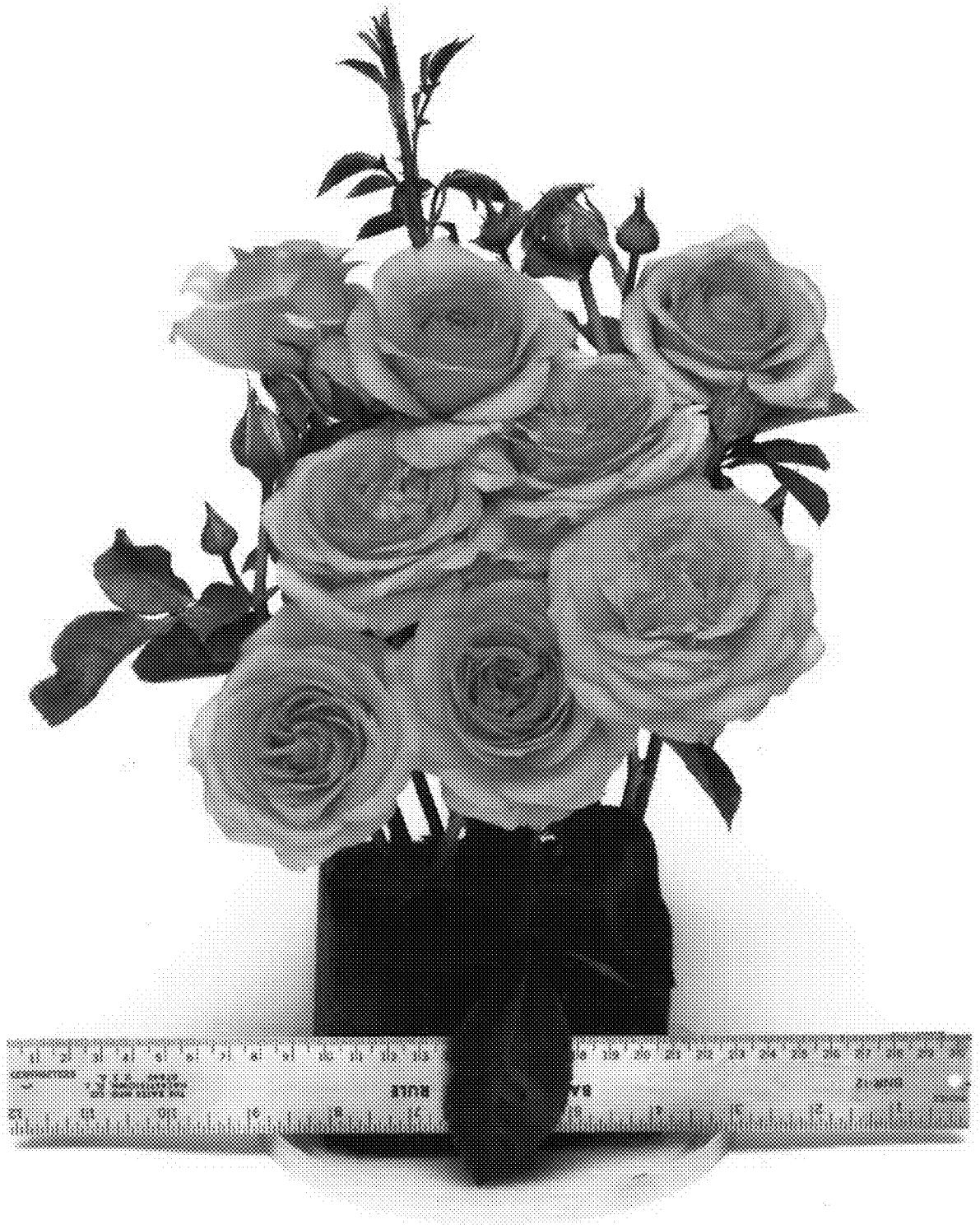

* * * * *